United States Patent [19]

Schaffner et al.

[11] 3,933,917

[45] Jan. 20, 1976

[54] PRODUCTION OF DIMETHYLBENZOPHENONE

[75] Inventors: Ernst Schaffner, Ludwigshafen; Heinz Eilingsfeld, Frankenthal; Manfred Patsch, Ludwigshafen, all of Germany

[73] Assignee: Badische Anilin- & Soda-Fabrik Aktiengesellschaft, Ludwigshafen (Rhine), Germany

[22] Filed: Aug. 29, 1973

[21] Appl. No.: 392,822

[30] Foreign Application Priority Data

Sept. 2, 1972 Germany.......................... 2243283

[52] U.S. Cl. ................. 260/591; 260/376; 260/517
[51] Int. Cl.² ....................................... C07C 49/76
[58] Field of Search..................... 260/376, 517, 591

[56] References Cited
UNITED STATES PATENTS
2,967,187    1/1961    Serres et al. ........................ 260/376

OTHER PUBLICATIONS

Rec. Trav. Chim. Pays–Bas, 79, pp. 790–793 (1960).

Olah, Friedel–Crafts and Related Reactions, III, Part I, pp. 4, 5, 8, 9, 39, 40, 43 (1964).

Primary Examiner—Lorraine A. Weinberger
Assistant Examiner—Jane S. Myers
Attorney, Agent, or Firm—Johnston, Keil, Thompson & Shurtleff

[57]    ABSTRACT

The production of anthraquinone-1-carboxylic acid by reacting a benzoyl halide with a tert.-butylxylene in the presence of ferric chloride, adding aluminum chloride, oxidizing the dimethylbenzophenone formed and cyclizing the resulting benzophenonedicarboxylic acid. The product is a starting material for the production of dyes and pesticides.

6 Claims, No Drawings

PRODUCTION OF DIMETHYLBENZOPHENONE

The invention relates to a process for the production of anthraquinone-1-carboxylic acid by the reaction of a benzoyl halide with a tert.-butylxylene in the presence of ferric chloride and then with an addition of aluminum chloride, followed by oxidation of the dimethylbenzophenone formed and cyclization of the resultant benzophenonedicarboxylic acid.

It is known that anthraquinone-1-carboxylic acid can be prepared from 3-benzoylphthalic acid or from 2-benzoylisophthalic acid by heating for a short time in sulfuric acid (Ann. 290 (1896), 231 et seq.; Ber. 30 (1897), 1115 et seq.) or by oxidation of 1-methylanthraquinone (J. Prakt.Chem.(2), 83 (1911), page 205, and German Pat. Nos. 259,365 259.365 and 539,100).

It is known from Ullmanns Encyklopädie der technischen Chemie, volume 7, pages 689 et seq. that the production of aromatic ketones can be carried out by Friedel-Crafts reaction of an acylatable aromatic compound with an acyl chloride in the presence of a stoichiometric amount or advantageously with an excess of aluminum chloride. Contrasted with alkylation with an alkyl halide, catalytic amounts are not sufficient and this is expressly stated on page 690, second paragraph. Other metal halides may be used instead of aluminum chloride, for example stannic chloride, boron fluoride and ferric chloride; reference is made however to the oxidizing and chlorinating side effects of ferric chloride which often occur (loc.cit. page 683).

It is known from Rec.Trav.Chim.Pays-Bas 79 (1960), pages 790 et seq. that 1,3-dimethyl-5-tert.-butylbenzene reacts with benzoyl chloride in nitrobenzene in the presence of aluminum chloride to form 2,6-dimethyl-4-tert.-butylbenzophenone. Similarly 2,6-dimethylbenzophenone can be prepared from 2,6-dimethyl-4-tert.-butyl-benzophenone by dealkylation in the presence of aluminum chloride in benzene. Reference is expressly made to the fact that benzoylation and elimination of the butyl group cannot be carried out in a combined two-stage process (page 791, 3rd paragraph). A single vessel process is also not achieved when another solvent, for example benzene, is used instead of nitrobenzene and varying amounts for aluminum chloride are used; side reactions, for example varying substitution of the benzoyl radical, migration of the alkyl group, incomplete elimination of the butyl group, result in a reaction mixture containing many heterogeneous components.

It is an object of the present invention to provide a novel process for producing anthraquinone-1-carboxylic acid, 2,3-dimethylbenzophenone and 2,6-dimethylbenzophenone in a simpler and more economical way and in better yields and higher purity.

We have found that anthraquinone-1-carboxylic acid is obtained advantageously by reacting a benzoyl halide in a first stage with a tert.-butylxylene of the general formula (I):

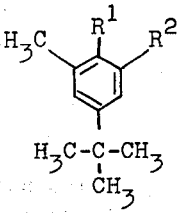

in which one of the two radicals $R^1$ and $R^2$ is hydrogen and the other radical is methyl in the presence of ferric chloride, and reacting the reaction mixture thus formed in the presence of aluminum chloride, oxidizing the dimethylbenzophenone of the general formula (II):

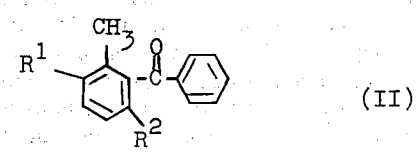

(II)

in which $R^1$ and $R^2$ have the above meanings in a second stage to form the benzophenone dicarboxylic acid and cyclizing this in a third stage.

We have further found that dimethylbenzophenones of the general formula (II) in which one of the two radicals $R^1$ and $R^2$ is hydrogen and the other methyl are obtained advantageously by reacting a benzoyl halide with a tert.-butylxylene of the general formula (I) in which one of the two radicals $R^1$ and $R^2$ is hydrogen and the other methyl in the presence of ferric chloride and reacting the reaction mixture thus formed in the presence of aluminum chloride.

The reaction may be represented by the following formulae:

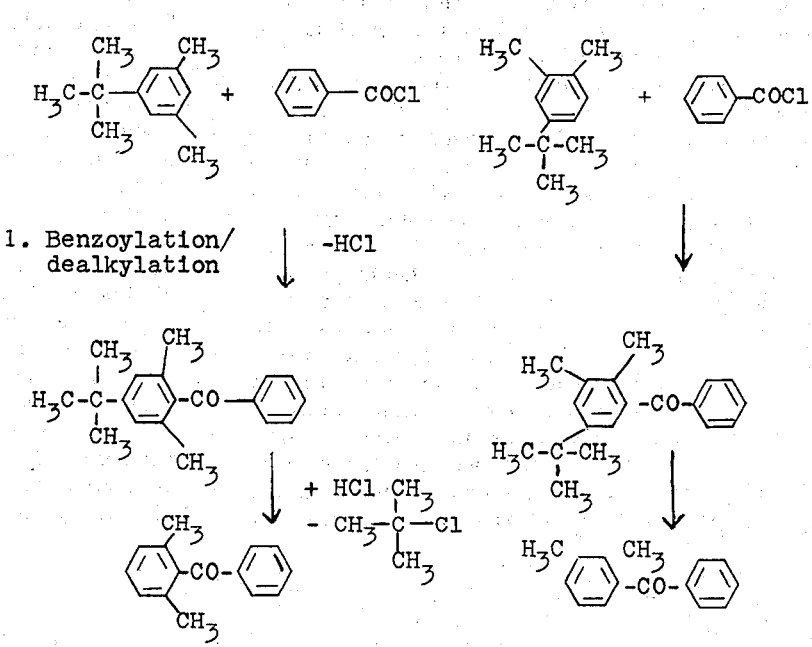

2. Oxidation

3. Ring closure

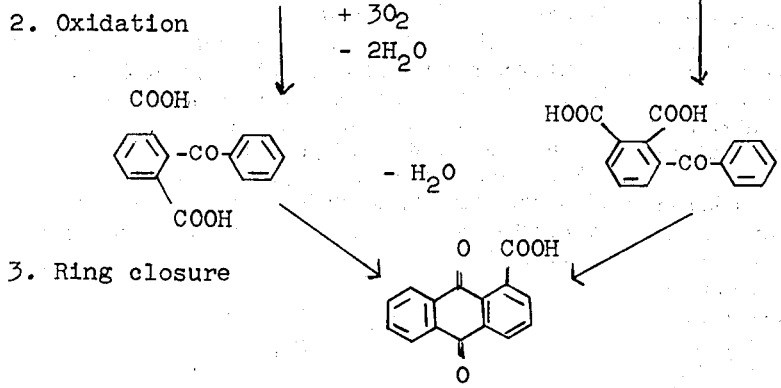

As compared with prior art methods the process of the invention gives anthraquinone-1-carboxylic acid, 2,3-dimethylbenzophenone and 2,6-dimethylbenzophenone in better yields and higher purity by a simpler and more economical method. It is surprising that it is possible to carry out a single-liquor benzoylation/-debutylation process and that not only nitrobenzene but other solvents as well may be used for the first stage of the reaction. Difficulties by additional chlorination or oxidation of the starting material, due to the presence of ferric chloride, do not occur to any appreciable extent if at all. Nor do side reactions which result in mixtures of heterogeneous components in the first stage. The combination of the three said reaction stages in the said sequence provides a simpler and more economical method, especially on a commercial scale, which permits continuous operation. This sequence of the stages moreover results in end products of good purity without the need for special purification. All these advantages of the process are surprising having regard to the prior art.

The starting material (I) may be 5-butyl-m-xylene, 4-tert.-butyl-o-xylene or a mixture of the two. Benzoyl iodide, benzoyl bromide and particularly benzoyl chloride are preferred benzoyl halides. The benzoyl halide and the starting material (I) may be reacted in the molar ratio or one component may be used in excess, as a rule the component to be acylated. The starting materials are preferably reacted in a ratio of from 1 to 6 moles and particularly from 1 to 4 moles of starting material (I) per mole of benzoyl halide.

The first stage of the reaction is generally carried out at a temperature of from −10°C to 300°C at atmospheric or superatomospheric pressure continuously or batchwise. A cascade of vessels may conveniently be used for continous reaction, although a pressure reactor is preferred. The range of temperature preferably chosen for the acylation step is from −10° to 220°C and particularly from −10° to 100°C, and that for the dealkylation is preferably from 30° to 150°C and particularly from 70° to 120°C. The first stage may be carried out with or without adding a solvent. If it is convenient to use a solvent it should be inert under the reaction conditions such as an aromatic hydrocarbon, for example benzene, nitrobenzene, trichlorobenzene, a chlorohydrocarbon such as methylene chloride, ethylene chloride, carbon tetrachloride or chloroform; carbon disulfide or an aliphatic hydrocarbon such as ligroin or petroleum ether. A suitable amount of solvent is from 1 to 20% by weight based on the starting material (I). The benzoylation may also be carried out in the absence of solvents or in the starting mixture itself as the solvent medium, solvent not being added until carrying out the debutylation. Accordingly solvent may be used at the beginning of the first stage and a further amount of the same or another solvent added when the debutylation is carried out or the debutylation may be carried may be carried out without such addition. When solvent is added both in the benzoylation and in the debutylation convenient amounts are from 40 to 60% by weight of solvent for the benzoylation and 400 to 700% by weight of solvent for the debutylation, based on starting material (I).

Ferric chloride and aluminum chloride may be used in an excess with reference to starting material (I) or in a stoichiometric amount, and conveniently in an amount of from 1 to 1.5 moles of ferric chloride and from 1 to 1.5 moles of aluminum chloride based on 1 mole of starting material (I) in the first stage. In a preferred embodiment the benzoylation is carried out with ferric chloride in a catalytic amount, preferably in the presence of from 0.5 to 7 and particularly from 1 to 3% weight of ferric chloride based on benzoyl halide. Amounts lying between the stoichiometric amount and the abovementioned catalytic amounts of ferric chloride may however be used. When a catalytic amount of ferric chloride is used temperatures of from −10° to +220°C, preferably from 80° to 220°C and particularly from 100° to 150°C are advantageous.

The procedure when carrying out the first stage batchwise may be that the reactants, the catalyst and any solvent are mixed in any sequence and as a rule the components are caused to react by heating. The benzoylation is usually over after from five to seven hours. The whole is then cooled if necessary to the preferred debutylation temperature, aluminum chloride and any solvent are added and the mixture is debutylated for from three to eight hours. In a preferred embodiment hydrogen chloride is added as well as aluminum chloride and conveniently in an amount of from 10 to 80 and preferably from 15 to 30% by weight based on aluminum chloride. It is advantageous to add the hydrogen chloride continuously up to the end of the debutylation. Dimethylbenzophenone formed is then isolated from the reaction mixture by a conventional method, for example by washing with water followed by distillation or by direct distillation of the reaction mixture. The debutylation mixture may also be poured onto a mixture of ice and mineral acid or onto ice-water, extracted with the said solvents and the extract distilled.

Elimination of the tert.-butyl group may also be carried out in the presence of an acceptor for the tert.-butyl group and aluminum chloride and the solvent itself may be the acceptor. Examples of acceptors for the tert.-butyl group are benzene, phenol or a phenol ether such as anisol or phenetol. Benzene is particularly preferred because it is cheap. The acceptor is generally used in an amount of from 200 to 1000, preferably from 400 to 700% by weight, based on starting material (I). The first stage of the reaction and the processing of the reaction mixture are carried out in the manner described above.

In the second stage of the reaction the 2,3-dimethylbenzophenone (II) or 2,6-dimethylbenzophenone (II) is oxidized with an oxidizing agent. The preferably inorganic oxidizing agent may be gaseous, solid or liquid. The following compounds may be used with advantage: chromium compounds such as potassium bichromate, ammonium bichromate, chromic acid, chromyl chloride; permanganates such as potassium permanganate, nitric acid and salts thereof, for example sodium nitrate, silver nitrate, potassium nitrate, lithium nitrate, calcium nitrate, magnesium nitrate, nickel nitrate, chromium nitrate, copper nitrate, cobalt nitrate, cerium nitrate, thorium nitrate, bismuth nitrate, iron nitrate and mercury nitrate. Oxygen or gases containing it, for example air, alone or using a catalyst, for example an oxide of iron, chromium, aluminum, molybdenum, vanadium, tungsten or zinc if desired together with an alkali metal oxide, and appropriate mixtures; bromine or bromides; cobalt, copper, manganese, lead, cerium, mercury, barium salts, for example the appropriate acetates, sulfates and chlorides; nickel, palladium, platinum, silver and zinc are also suitable as oxidizing agents. The oxidizing agent is advantageously used in a ratio of from 0.001 to 0.5 mole and preferably from 0.05 to 0.1 mole of starting material (II) and when oxygen is used as oxidizing agent in a ratio of from 0.05 to 2 moles of oxygen per mole of starting material (II). The oxidation is generally carried out at a temperature of from $+40°$ to $+250°C$ and preferably at from $+50°C$ at atmospheric or superatomospheric pressure, continously or batchwise. Organic solvents which are inert under the reaction conditions may be used in the oxidation; examples are aliphatic hydrocarbons such as n-pentane, n-heptane, cycloaliphatic hydrocarbons such as cyclohexane, aliphatic carboxylic acids such as acetic acid, propionic acid, valeric acid, aromatic hydrocarbons such as chlorobenzene, dichlorobenzene, trichlorobenzene or mixtures of two or more of these.

The second stage of the reaction may be carried out as follows: Any apparatus in which the starting material can be brought into intimate contact with the starting material and if necessary with the catalyst may be used as the reactor, in the case of liquid mixtures such as the said solutions for example a trickling tower, a bubble column, a cascade reactor, packed column, sieve-plate column, Oldershaw column, glass tray column, bubble tray column or valve plate column. A mixture of starting material (II), oxidizing agent and if desired solvent may also be reacted continuously or batchwise for from 6 to 8 hours in a stirred vessel or cascade of stirred vessels at the reaction temperature. In the case of solid oxidizing agents and any solid catalysts used the starting material (II) may be passed in liquid or gaseous condition at the reaction temperature for example over a bed of catalyst in a tubular reactor. Batchwise mixtures of starting material (II) and solid oxidizing agent may be reacted in a similar way to that used in the case of liquid mixtures. Oxidizing agent and any catalyst used may be suspended in liquid starting material (II) of fluidized (fluidized bed). After the oxidation the benzophenone dicarboxylic acid formed is isolated from the oxidation mixture by a conventional method, for example by dissolving it in caustic alkali solution, precipitation by acidifying the solution with a dilute mineral acid and filtration.

An advantageous embodiment of the second stage makes use of chromium (VI) compounds and/or nitric acid as oxidizing agents. The oxidation is carried out as a rule at a temperature of from 50° to 250°C and preferably at from 90° to 110°C. Atmospheric pressure or superatmospheric pressure may be used, for example a pressure of up to 100 atmospheres, generally the autogeneous pressure set up under the reaction conditions. The reaction may be carried out continuously or batchwise.

The starting material (II) is reacted with chromium (VI) compounds in less than eight times, preferably from four to six times, the stoichiometric amount with reference to the starting material (II). The following chromium (VI) compounds are suitable: monochromic acid, polychromic acid, for example dichromic acid, trichromic acid, tetrachromic acid and their anhydrides and salts. The salts used are advantageously alkali metal or alkaline earth metal chromates and bichromates, particularly sodium or potassium chromate or bichromate.

The reaction is carried out as a rule in the presence of a solvent such as an organic acid and preferably an inorganic acid. It is advantageous to use sulfuric acid, conveniently in the form of a from 10 to 80% by weight aqueous solution and/or nitric acid, conveniently in the form of a from 10 to 65% by weight aqueous solution. The reaction is generally carried out in a ratio of from 1.5 to 50 moles of sulfuric acid (calculated as 100%) per mole of chromium (VI) compound.

Oxidation with nitric acid is conveniently carried out at a temperature of from 50° to 250°C and preferably from 110° to 230°C. The starting material (II) is reacted with nitric acid in a stoichiometric amount or in excess, preferably in a molar ratio of 1 mole of starting material to from 6 to 30 and particularly from 6 to 20 moles of nitric acid. Aqueous nitric acid solutions containing from 2 to 50,% preferably from 5 to 40% and particularly from 5 to 30% by weight of nitric acid are generally used for the reaction. The optimum concentration and amount of nitric acid for a given temperature can easily be determined by preliminary tests. The oxidation may be carried out as follows: a mixture of starting material (II) and nitric acid of the said concentration is kept at the reaction pressure in an autoclave for about 15 minutes to 2 hours at the oxidation temperature. The reaction mixture is then cooled and processed in the manner described above.

In another preferred embodiment of stage 2 the starting material is reacted with oxygen alone or mixed with gas inert under the reaction conditions, for example nitrogen or carbon dioxide, the oxygen as a rule being used in a ratio of from 3 to 50 moles, preferably from 4 to 20 moles of oxygen to 1 mole of starting material (II). The oxidation is carried out in the presence of a heavy metal catalyst, in many cases of compounds of metals of group 7 or 8 of the Periodic Table. Preferred catalyst are salts of iron, nickel, chromium, tin, vanadium, molybdenum, cadmium, lead, cerium, palladium and particularly cobalt or manganese. These metal salts may be of inorganic or organic nature, for example perchlorates, chlorides, bromates, propionates, butyrates, phthalates, naphthenates or particularly bromides or acetates. Mixtures of the said catalysts may also be used, for example manganese bromide or acetate together with ammonium molybdate, tungstic acid or cobalt acetate. The catalyst is generally used in an amount of from 0.1 to 10% by weight based on starting material (II).

In addition to the heavy metal catalyst use is made in many cases of bromine or bromides as activators. Examples of such bromides are those of sodium, potassium, ammonium, calcium, barium, antimony, tin, aluminum and magnesium or particularly of cobalt, lead or manganese. Mixtures of the same or compounds which form such bromides with the heavy metal catalyst during the reaction may also be used, for example hydrogen bromide or tetrabromoethane. Combinations of a cobalt or manganese acetate with a cobalt or manganese bromide are preferred. Generally the reaction is carried out in the presence of from 0.1 to 15% by weight of bromine or a bromide based on the starting material (II).

Peroxides or compounds which form peroxides may be present in the reaction as activators in addition to heavy metal catalysts and possibly bromides; examples are cobalt acetate and acetaldehyde or cobalt bromide, manganese bromide and methyl ethyl ketone. Examples of preferred peroxides are ozone, xylene hydroperoxide, perbenzoic acid and preferred compounds which form peroxides are for example methyl ethyl ketone, acetaldehyde, cyclohexanone, propionaldehyde, n-butyraldehyde, isobutyraldehyde, methyl n-propyl ketone, diethyl ketone, 2,4-pentane-dione, 2,5-hexanedione, toluic aldehyde, butanols, and butane. They are used as a rule in an amount of from 0 to 100% molar based on starting material (II).

The reaction is carried out batchwise or continuously at elevated temperature, generally of from 50° to 250°C and preferably from 80° to 200°C and at superatmospheric pressure, generally at from 1 to 100 and preferably from 1.3 to 25 atmospheres. Alkanoic acids, preferably of two to four carbon atoms are used as solvents, for example acetic acid or propionic acid, generally in an amount of from 100 to 10,000% molar based on starting material (II). The oxidation is carried out as follows: starting material (II), heavy metal catalyst, solvent and activator are introduced into a reactor and oxidized for 3 to 5 hours at the said temperature and at the oxidation pressure. Oxygen or air is conveniently supplied uniformly over the entire reaction period or replenished in the reactor at the rate at which oxygen is used up. The reaction mixture of the preferred embodiment of the second reaction stage is then processed in the manner described above.

In the third stage of the reaction the 2,3-benzophenone dicarboxylic acid or 2,6-benzophenone dicarboxylic acid of the general formula (III):

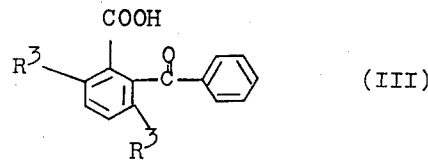

in which $R^3$ is in one case hydrogen and in the other case carboxyl, which has been formed is cyclized, conveniently in the presence of a mineral acid such as sulfuric acid or polyphosphoric acid.

Suitable polyphosphoric acids are the linear polyphosphoric acids of the general formula $H_{n+2}P_{2n}O_{3n+1}$ obtainable by the thermal dehydration of orthophosphoric acid and having a degree of condensation of up to $n = 15$, preferably those having from 72 to 88% and particularly from 76 to 83% by weight of $P_2O_5$. Amounts of from 300 to 1000% by weight of polyphosphoric acid of the said $P_2O_5$-content, based on starting material (III) are suitable. Solvents such as N-methylpyrrolidone, nitrobenzene or high boiling point alkanols such as glycol monomethyl ether may be used, conveniently in an amount of from 200 to 500% by weight (based on starting material (III) in addition to the polyphosphoric acid.

Cyclization is generally carried out in the presence of sulfuric acid conveniently of from 95 to 98% by weight strength. Suitable amounts based on starting material (III) are from 300 to 1000% and particularly from 400 to 600% by weight of sulfuric acid. Cyclization is generally carried out at a temperature of from 40° to 220°C and preferably from 120° to 160°C at atmospheric or superatmospheric pressure, continuously or batchwise, Cyclization may be carried out as follows: a mixture of starting material (III) and acid is kept for 1 hour to 2 hours at cyclization temperature. Then the end product is separated from the reaction in a conventional way, for example by mixing with water and filtration.

Anthraquinone-1-carboxylic acid which can be prepared according to the process of the invention is a valuable starting material for the production of dyes and pesticides. Reference may be made to Ullmanns Encyklopädie der technischen Chemie, 3, pages 681 et seq for details of such use. The following Examples illustrate the invention. Parts specified in the Examples are by weight.

EXAMPLE 1 a. Benzoylation and dealkylation 81 parts of 5-tert.-butyl-m-xylene and 70 parts of benzoyl chloride are kept with 2.4 parts of ferric chloride for three hours at from 100° to 120°C. The whole is cooled to 25°C and 600 parts of benzene and 100 parts of aluminum chloride are added. 20 parts of hydrogen chloride is passed into the mixture during six hours at 70° to 80°C. The mixture is poured onto 1000 parts of ice-water. The organic phase which forms is separated and 77 parts (73.3% of theory) of 2,6-dimethylbenzophenone having a boiling point of 122° to 125°C is isolated by distillation at 0.3 mm Hg.

b. Oxidation

A mixture of 10 parts of 2,6-dimethylbenzophenone, 80 parts of propionic acid, 0.5 part of cobalt acetate and 0.25 part of cobalt bromide is oxidized at 125°C and 1.3 atmospheres with 36 parts of air during three hours. The mixture is concentrated and the residue is extracted with 80 parts of dilute caustic soda solution (8% by weight). After filtration the benzophenone-2,6-dicarboxylic acid is precipitated from the filtrate with 100 parts of hydrochloric acid (7% by weight). 11 parts of benzophenone-2,6-dicarboxylic acid is obtained having a melting point of 233° to 235°C.

a. Cyclization 5 parts of benzophenone-2,6-dicarboxylic acid is heated in 25 parts of 97% by weight sulfuric acid for 90 minutes at 145° to 150°C. After the solution has been cooled it is poured onto 150 parts of water. Anthraquinone-1-carboxylic acid is precipitated. It is suction filtered, washed with water and dried. 3.8 parts of end product is obtained with a melting point of 288° to 290°C.

EXAMPLE 2 a. Benzoylation and dealkylation 81 parts of 5-tert.-butyl-m-xylene, 140.5 parts of benzoyl chloride and 2.4 parts of ferric chloride are heated for 3 hours at 100°C. 70 parts of benzoyl chloride is distilled off at 20 mm. 500 parts of benzene and 100 parts of aluminum chloride are added and hydrogen chloride is passed in for five hours at 70° to 80°C. After having been processed analogously to Example 1, 85 parts (81% of the calculated amount) of 2,6-dimethylbenzophenone having a boiling point of 110° to 114°C at 0.25 mm is obtained.

b. Oxidation 21 parts of 2,6-dimethylbenzophenone in 120 parts of water has 40 parts of 100% by weight nitric acid added to it and the whole is heated in an autoclave for 6 hours at 170°C. It is then evaporated. The residue is taken up with 200 parts of dilute caustic soda solution (8% by weight). The solution is filtered and the benzophenone-2,6-dicarboxylic acid is precipitated from the filtrate with 220 parts of dilute hydrochloric acid (7% by weight). It is suction filtered, washed with water and dried. 23.2 parts of the dicarboxylic acid is obtained, melting point 228° to 231°C.

c. Ring closure

Cyclization is carried out analogously to Example 1. 3.8 parts of end product having a melting point of 288° to 290°C is obtained.

EXAMPLE 3 a. Benzoylation and dealkylation

This is carried out as described in Example 2.

4.2 parts of 2,6-dimethylbenzophenone is suspended in 21 parts of glacial acetic acid and 30 parts 0f 60% by weight sulfuric acid and at 70°C 12 parts of sodium bichromate (dissolved in 40 parts by volume of 50% by weight sulfuric acid) is gradually added within 2 hours. After another 2 hours at 80°C the mixture is poured onto 200 parts of ice. The organic phase formed is separated and taken up in 100 parts of dilute caustic soda solution (8% by weight). The solution is filtered and acidified with 150 parts of dilute hydrochloric acid (7% by weight). The precipitated acid is filtered off, washed with water and dried. 3.6 parts of benzophenone-2,6-dicarboxylic acid is obtained having a melting point of 235° to 237°C.

c. Cyclization

Cyclization is carried out as described in Example 1. 3.8 parts of end product is obtained having a melting point of 288° to 290°C.

We claim:

1. A process for the production of dimethylbenzophenone of the formula

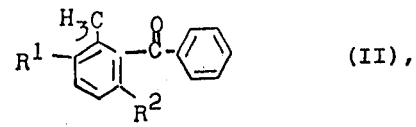

in which one of the two radicals $R^1$ and $R^2$ is hydrogen and the other is methyl, which process comprises:

a. reacting a benzoyl halide in a first benzoylation step with a tert.-butylxylene of the formula

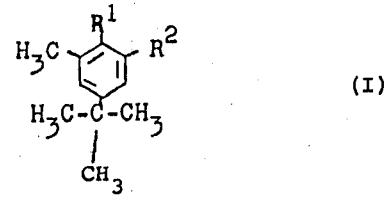

in which one of $R^1$ and $R^2$ is hydrogen and the other is methyl, in the presence of a catalytic amount of about 0.5 to 7% by weight of ferric chloride, with reference to the benzoyl halide, at a temperature of −10°C. to +220°C.; and b. reacting in a second dealkylation step the reaction mixture thus formed in said first step in the presence of about 1 to 1.5 moles of aluminum chloride per mole of the initial compound (I) at a temperature of 30°C. to 150°C.

2. A process as claimed in claim 1 in which both steps (a) and (b) are carried out in the presence of an inert solvent.

3. A process as claimed in claim 1 wherein the benzoylation step (a) is carried out with 1 to 3% by weight of ferric chloride with reference to the benzoyl halide.

4. A process as claimed in claim 1 wherein the dealkylation step (b) is carried out in the additional presence of an acid acceptor for the tert.-butyl group, said acceptor being selected from the group consisting of benzene, phenol, anisol and phenetol.

5. A process as claimed in claim 1 wherein the benzoylation step (a) is carried out at about −10°C. to 100°C. and the dealkylation step (b) is carried out at about 70°C. to 120°C.

6. A process as claimed in claim 1 carried out with from 1 to 6 moles of starting material (I) per mole of benzoyl halide.

* * * * *